(12) United States Patent
Choi et al.

(10) Patent No.: US 8,136,981 B2
(45) Date of Patent: Mar. 20, 2012

(54) HEAT TRANSFER EVALUATING APPARATUS

(75) Inventors: Cheol Choi, Daejeon (KR); Je-Myung Oh, Daejeon (KR); Shin-Pyo Lee, Yongin-si (KR); Mi-Hee Jung, Daejeon (KR)

(73) Assignee: Korea Electric Power Corporation

( * ) Notice: Subject to any disclaimer, the term of this patent is extended or adjusted under 35 U.S.C. 154(b) by 696 days.

(21) Appl. No.: 12/262,218

(22) Filed: Oct. 31, 2008

(65) Prior Publication Data

US 2009/0296772 A1 Dec. 3, 2009

(30) Foreign Application Priority Data

May 30, 2008 (KR) .................. 10-2008-0051188

(51) Int. Cl.
*G01N 25/18* (2006.01)
*G01K 13/02* (2006.01)
(52) U.S. Cl. .......................... 374/43; 374/135
(58) Field of Classification Search .............. 374/43, 374/29, 30, 44, 135
See application file for complete search history.

(56) References Cited

U.S. PATENT DOCUMENTS

| 4,154,088 | A  | * | 5/1979 | Werner ..................... 73/28.01 |
| 4,352,290 | A  | * | 10/1982 | Neils ......................... 374/110 |
| 4,779,673 | A  | * | 10/1988 | Chiles et al. ................. 165/45 |
| 7,209,355 | B2 | * | 4/2007 | Koga et al. ................... 361/699 |
| 7,390,428 | B2 | * | 6/2008 | Davidson et al. .............. 252/70 |
| 2005/0105583 | A1 | * | 5/2005 | Xiao et al. ..................... 374/29 |
| 2005/0175769 | A1 | * | 8/2005 | Kunugi et al. ................ 427/58 |
| 2006/0062273 | A1 | * | 3/2006 | Egolf et al. .................... 374/44 |
| 2007/0085054 | A1 | * | 4/2007 | Lin ............................... 252/70 |
| 2007/0127550 | A1 | * | 6/2007 | Liu et al. ..................... 374/147 |
| 2007/0237202 | A1 | * | 10/2007 | Li ................................. 374/147 |
| 2010/0329299 | A1 | * | 12/2010 | Choi et al. ..................... 374/43 |
| 2011/0122915 | A1 | * | 5/2011 | Wang et al. .................... 374/44 |

\* cited by examiner

*Primary Examiner* — Christopher Fulton
(74) *Attorney, Agent, or Firm* — McDermott Will & Emery LLP

(57) ABSTRACT

Disclosed is a heat transfer evaluation apparatus of a nanofluid including: a long pipe formed as a circular pipe; a rubber tube connected to one end of the long pipe to surround the outer surface of the long pipe; a short pipe communicated through the rubber tube; and a hot wire sensor formed of a metal hot wire at one end of the short pipe.

6 Claims, 10 Drawing Sheets

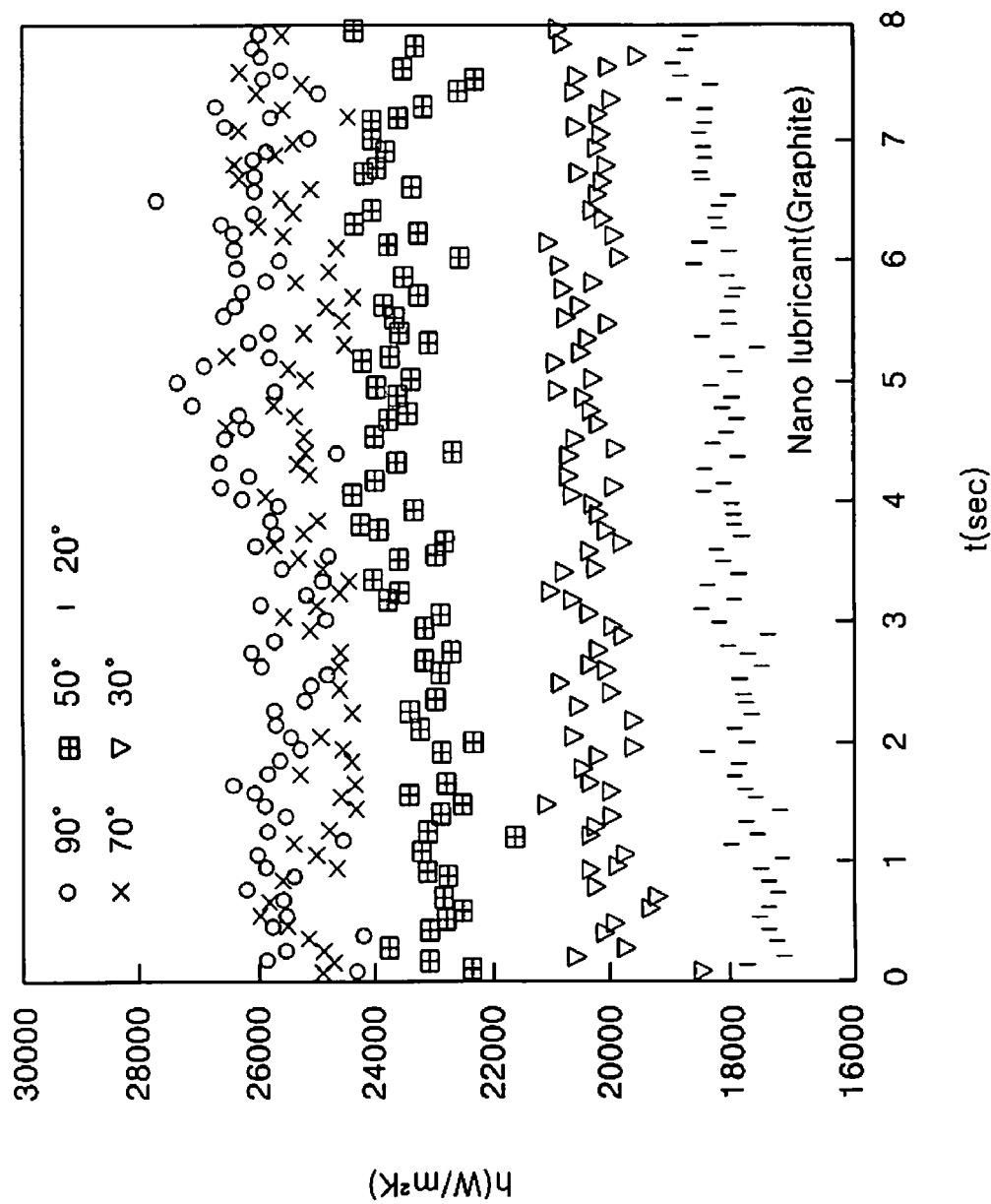

HEAT TRANSFER EVALUATING APPARATUS

PRIORITY

This application claims priority from and the benefit of Korean Patent Application No. 10-2008-0051188, filed on May 30, 2008, which is hereby incorporated by reference for all purposes as if fully set forth herein.

BACKGROUND OF THE INVENTION

1. Field of the Invention

Disclosed exemplary embodiments are directed to a heat transfer evaluating apparatus for a nano-fluid, and more specifically, to an apparatus that may determine the utility of a nano-fluid having a heat transfer improvement effect by measuring a convective heat transfer coefficient of the nano-fluid under flow conditions of the nano-fluid.

2. Description of the Related Art

Nano-fluids refer to colloidal compound fluids whose heat transfer capacity has been improved by adding a tiny amount of nano-size solid particles, whose thermal conductivity is significantly high, to a fundamental heat transfer fluid such as water, ethylene glycol, etc. to raise the thermal conductivity, thus improving the overall heat transfer capacity. Recently, a study has been intensively conducted domestically and internationally with respect to production, thermal property measurement, natural and forced convective heat transfer and boiling heat transfer of the nano-fluids.

In determining the heat capacity of nano-fluids, it has been primarily determined by measuring the thermal conductivity of the nano-fluids in the static state whether to be able to improve the heat transfer capacity of the nano-fluids. However, the addition of the nano-particles to the fundamental heat transfer fluid is generally accompanied with increase in viscosity as well as improvement of thermal conductivity. If the thermal conductivity of the nano-fluids has been improved but more pump force is required to drive the fluids, it needs to be determined whether to use the nano-fluids by calculating the whole expenses taking into consideration the heat transfer and necessary dynamic force. Accordingly, an experiment for convective heat transfer is required to make final determination on the heat capacity of samples of the nano-fluids.

A duplicate-pipe heat exchanger or an internal flowing apparatus using a heated pipe may be considered as a typical convective heat transfer coefficient experiment apparatus. However, such an experiment apparatus is complicated and large in volume because of even including peripherals such as a constant-temperature tub and a pump. Accordingly, there exist diverse difficulties in evaluating the convective heat transfer capacity of the nano-fluids.

And, the convective heat transfer experiment requires more expenses and time in contrast to the thermal conductivity measurement that is executed in the static state, and has a problem that many errors may be sometimes involved in the convective heat transfer coefficient calculated finally.

For instance, there could be considered problems such as time and expenses required to secure such a sufficient amount of nano-fluid samples to fill the inside of the apparatus, difficulties in washing the inside of the apparatus when the samples are exchanged, a long time taken to make the apparatus reach the steady state, and increase in uncertainty that could be involved in the convective heat transfer coefficient when the accuracy of the acquired data and thermal losses caused during the measurement process are not exactly calculated.

There is a need of providing a new apparatus different from existing apparatuses in terms of expenses and environmental problems caused when the samples are disposed.

SUMMARY OF THE INVENTION

According to an exemplary embodiment, there is provided an apparatus that may suggest the degree of improvement in a convective heat transfer coefficient rapidly and exactly regarding the produced nano-fluid samples to determine the utility as a high-efficiency heat transfer medium.

According to an exemplary embodiment, there is a heat transfer evaluation apparatus of a nano-fluid including: a long pipe formed as a circular pipe; a rubber tube connected to one end of the long pipe to surround the outer surface of the long pipe; a short pipe communicated through the rubber tube; and a hot wire sensor formed of a metal hot wire at one end of the short pipe.

The heat transfer evaluation apparatus of nano-fluids according to the exemplary embodiments allows for a rapid convective heat transfer experiment that is impossible to make in large-size apparatuses, thus saving lots of expenses and time required to produce the samples in the early stage of a small amount of nano-fluids.

In addition, the heat transfer evaluation apparatus may make an exact comparison on the schematic change in viscosity of the produced nano-fluids by measuring and comparing the transfer time of pure fluids because of being capable of acquiring the transfer time of fluids as data together with the convective heat transfer coefficient during the measurement experiment.

BRIEF DESCRIPTION OF THE DRAWINGS

The above and other features of the present disclosure will be described in reference to certain exemplary embodiments thereof with reference to the attached drawings in which:

FIGS. 7A, 7B, and 7C are views illustrating results of an experiment according to an exemplary embodiment, which is made with respect to three types of samples including another pure lubricant, a nano-lubricant mixed with CNT, and a nano-lubricant mixed with graphite, with the slope of the long pipe changed.

DETAILED DESCRIPTION OF THE PREFERRED EMBODIMENTS

Figure 1:
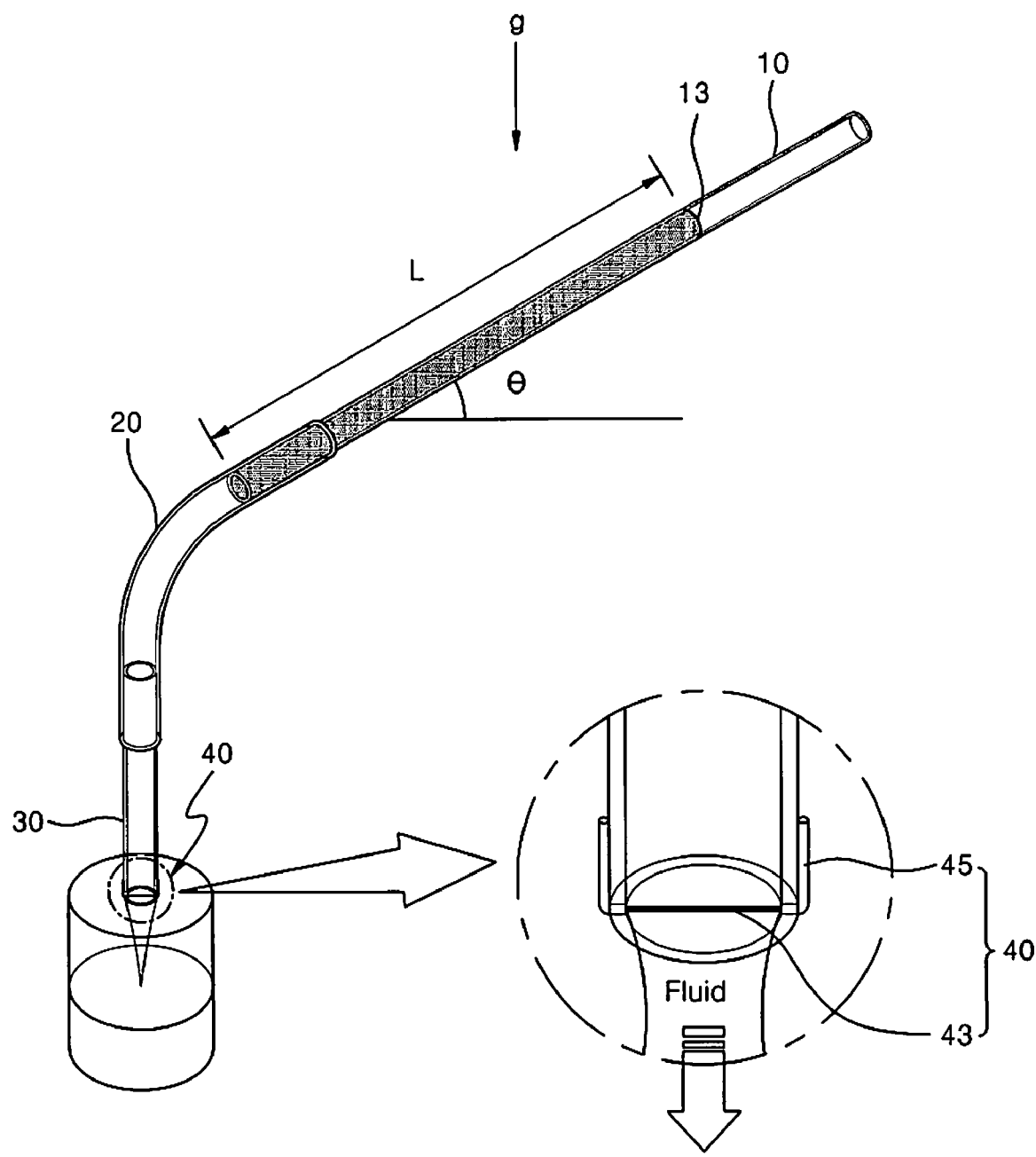
FIG. 1 is a view schematically illustrating a measurement apparatus according to an exemplary embodiment.

Reference will now be made in detail to exemplary embodiments, examples of which is are illustrated in the accompanying drawings, wherein like reference numerals refer to the like elements throughout. The embodiments are described below in order to explain the present disclosure by referring to the figures.

Hereinafter, exemplary embodiments will be described with reference to accompanying drawings.

FIG. 1 is a view schematically illustrating a measurement apparatus according to an exemplary embodiment.

There is suggested in the exemplary embodiment a nano-fluid convective heat transfer coefficient measurement apparatus that utilizes the fluid flow in a circular pipe by free fall and forced convective heat transfer phenomenon around a tiny hot wire.

Referring to FIG. 1, the nano-fluid convective heat transfer coefficient measurement apparatus may include a long pipe 10, a rubber tube 20, a short pipe 30, and a hot wire sensor 40.

The long pipe 10 may be a circular pipe that is made of a material such as acrylic, with the inner diameter of 7 mm, the outer diameter of 10 mm, and the wall thickness of 1.5 mm. And, the long pipe 10 may have the length of about 1 m. Further, an indication line 13 is marked at a location which is spaced by 75 cm from one end of the long pipe 10 in the opposite direction of gravity to indicate the initial location of a fluid.

The rubber tube 20 has the same inner diameter as that of the long pipe 10, and may be formed of an elastic, smooth material. Accordingly, the rubber tube 20 may be coupled to the long pipe 10 at one end of the long pipe 10 to surround the outer surface of the long pipe 10 by press-fitting.

The short pipe 30 is communicated with the long pipe 10 through the press-fitted rubber tube 20. Accordingly, the rubber tube 20 is press-fittingly coupled with the short pipe 30 at one end of the short pipe 30 to surround the outer surface of the short pipe 30. And, the short pipe 30 may be formed of a material such as acrylic, with the wall thickness of 1.5 mm that is equal to that of the long pipe 10, inner diameter of 7 mm, and outer diameter of 10 mm. The short pipe 30 may have the length of about 15 cm.

Even though the short pipe 30 is fixed, the rubber tube 20 coupled with the long pipe 10 that is freely movable is bent and therefore its slope (θ) may be adjusted against gravity. The falling velocity of the fluid, i.e. the velocity of the fluid in the pipe, may be changed according to the slope.

The hot wire sensor 40 may be a metal hot wire such as a platinum hot wire 43 or nichrome wire that is shaped as a cylinder at one end of the short pipe 30, with the diameter of 50 μm and length of 7 mm. A thick copper wire 45 may be connected between both ends of the platinum hot wire 43. The copper wire 45 is attached onto the outer surface of the short pipe 30 so that the platinum hot wire 43 is located across the center of the inner diameter of the short pipe 30. The hot wire sensor 40 corresponds to a heated cylinder. And, the hot wire sensor 40 equivalently operates as a metal resistor.

In addition, the nano-fluid convective heat transfer coefficient measurement apparatus may further include a standard resistor (not shown), a power supply (not shown), and a data acquisition device (not shown) that may acquire measured data.

Figure 2:
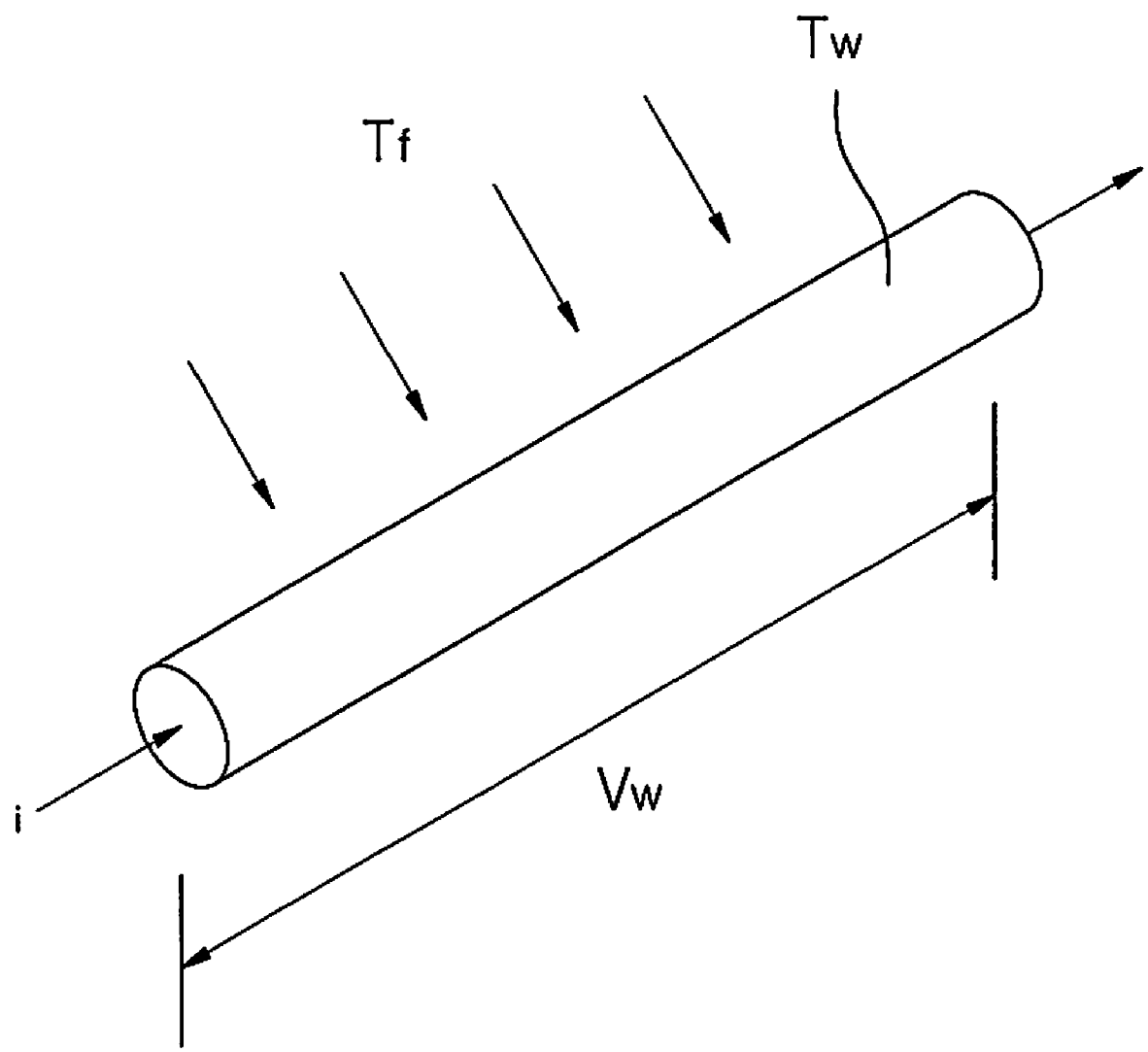
FIG. 2 is a view schematically illustrating a convective heat transfer phenomenon of a fluid flowing between the heated platinum hot wire and its surroundings.

FIG. 2 is a view schematically illustrating a convective heat transfer phenomenon of a fluid flowing between the heated platinum hot wire and its surroundings.

Referring to FIG. 2, "i" refers to a current flowing across the platinum hot wire 43, "A" to the surface area of the platinum hot wire 43, and "Tf" to the temperature of an external fluid. "H" is the convective heat transfer coefficient that represents the heat transfer capacity, and this may vary with the velocity and type of a fluid.

A voltage Vw is applied across the platinum hot wire 43 which is under fluid flow. Then, current i which corresponds to flow of electrons is created by an external force, i.e. voltage. At this time, the movement of electrons is interrupted due to collisions with atomic nuclei, bound electrons, and internal impurities that exist in the conductor. While electrons overcome such interruption and move in one direction, frictional heat and thermal vibration of atoms are generated. As such, joule heat q is generated at the conductor by the flow of currents, and the generated heat is transferred to the fluid by convection.

When the amount of heat generated at the platinum hot wire 43 is balanced with the convective heat transfer to the fluid, the following equation 1 is satisfied:

$$q = V_w \cdot i = hA(T_w - T_f)$$ [Equation 1]

It can be seen from the above Equation 1 that the operation temperature Tw of the platinum hot wire 43 is determined according to joule heat q, convective heat transfer coefficient h, and temperature Tf of the external fluid.

Accordingly, cooling is actively performed around the platinum hot wire 43 and the convective heat transfer coefficient h increases under the constant joule heat q by change of the condition of external heat flow, thus lowering the temperature of the platinum hot wire 43.

The fluid being changed in velocity to 10 m/s while being kept stationary, the fluid being changed from air to water, or the increase in thermal conductivity by introduction of a nano-fluid to the system on behalf of the fundamental fluid all correspond to variation in the external heat flowing condition that the platinum hot wire 43 may experience.

On the contrary, the convective heat transfer coefficient h may be replaced by the following Equation 2 under the given condition as long as the amount of heat and temperature of the metal hot wire and its surrounding fluids may be known by measuring voltage and current across the platinum hot wire 43.

$$h = \frac{q}{A(T_w - T_f)}$$ [Equation 2]

The method of measuring the convective heat transfer coefficient h outside the platinum hot wire 43 based on the above principle has been introduced in a heat transfer-related textbook as flow around a heated cylinder in cross flow.

The platinum hot wire 43 used in the exemplary embodiment corresponds to a cylinder having very short diameter as a platinum wire.

Voltage Vw, current i flowing across the platinum hot wire 43, and external fluid temperature Tf are necessary to know in order to calculate the convective heat transfer coefficient h under the given heat flow condition. The Tf of samples is measured by using a is standard thermometer prior to an experiment. Vw, i, and Tw associated with the platinum hot wire 43 may be measured by a voltage dividing circuit that will be described later with reference to FIGS. 3 and 4.

Figure 3:
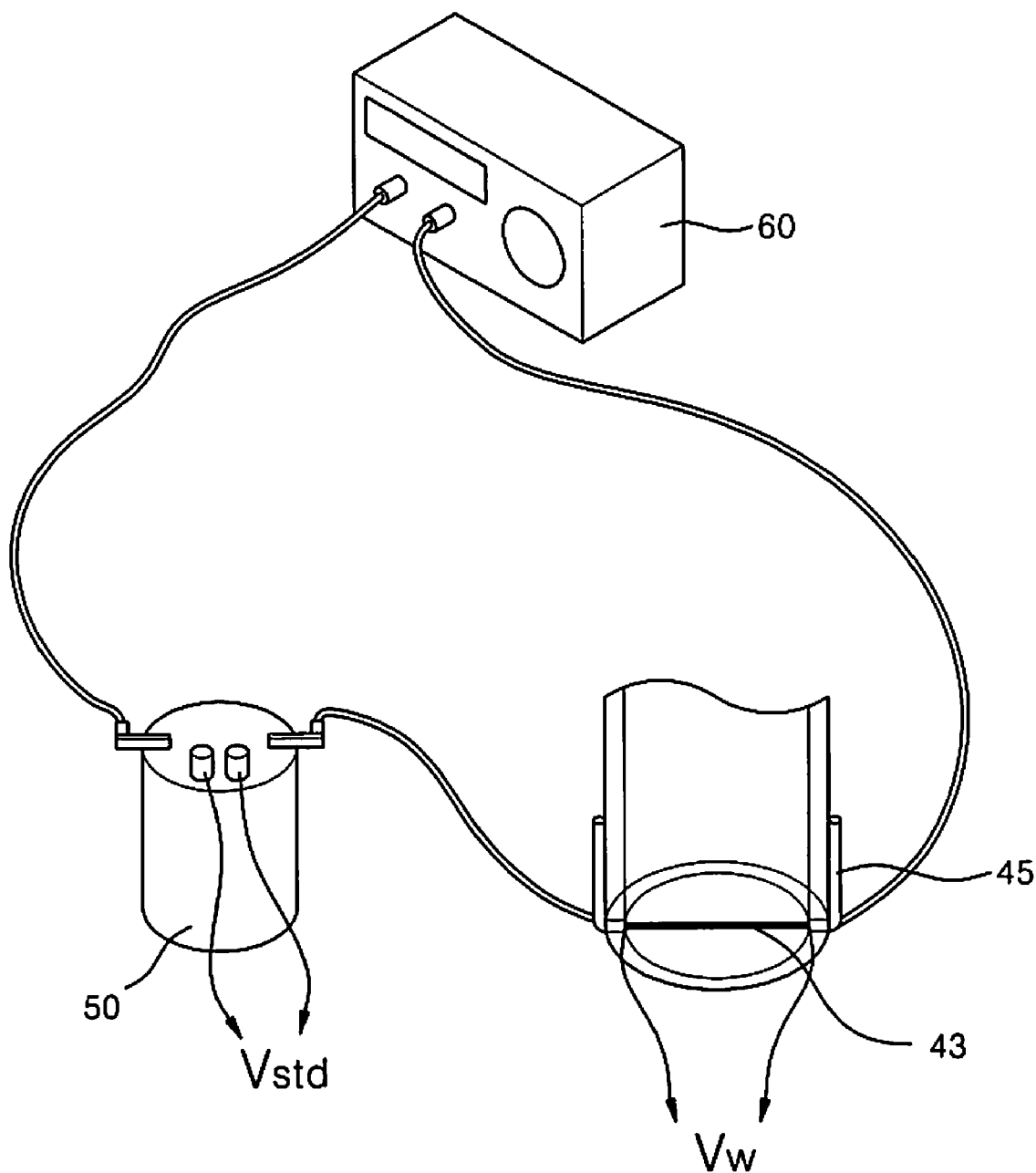
FIG. 3 is a view schematically illustrating connection between a standard resistor (STD) and a platinum hot wire.
Figure 4:
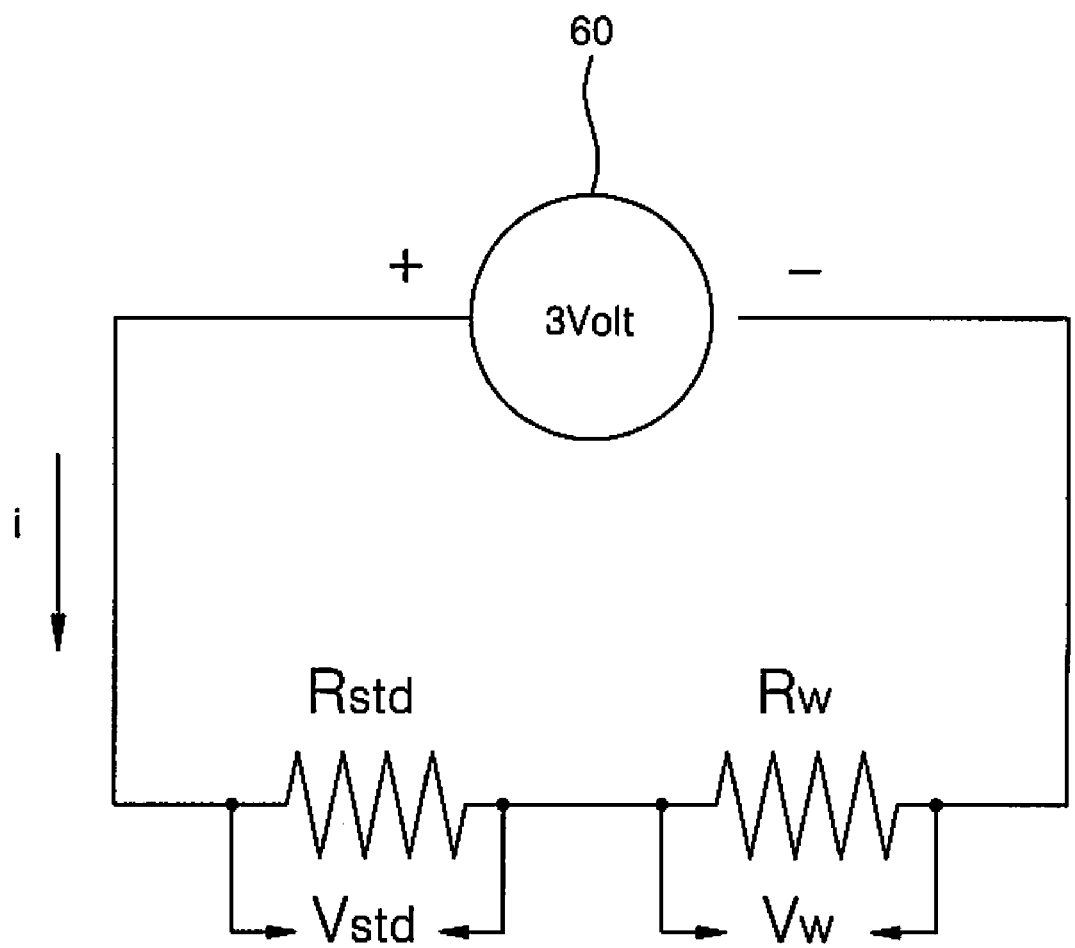
FIG. 4 is a view illustrating an equivalent circuit of the construction shown in FIG. 3.

FIG. 3 is a view schematically illustrating connection between a standard resistor (STD) and a platinum hot wire, and FIG. 4 is a view illustrating an equivalent circuit of the construction shown in FIG. 3.

Referring to FIGS. 3 and 4, the resistance of the standard resistor 50 is Rstd and a voltage applied across the standard resistor 50 is Vstd. Since the standard resistor 50 and the platinum hot wire 43 are connected in series with each other, current flowing across the standard resistor 50 is identical to current flowing across the platinum hot wire 43, and this satisfies the following Equation 3 by ohm's law.

$$\frac{V_w}{R_w} = \frac{V_{std}}{R_{std}} \quad \text{[Equation 3]}$$

The resistance Rw of the platinum hot wire 43 may be calculated by replacing Equation 3 by Equation 4.

In other words, Rw may be obtained using the known standard resistance Rstd by is measuring the voltage across both ends of the standard resistor and the voltage between both ends of the platinum hot wire.

Such a resistance-temperature relationship as equation 5 is satisfied between the resistance and temperature of the platinum wire.

$$R_w = \frac{V_w}{V_{std}} R_{std} \quad \text{[Equation 4]}$$
$$R_w = R_0(1 + aT_w)$$
or,
$$T_w = \frac{(R_w - R_0)}{R_0 a} \quad \text{[Equation 5]}$$

Accordingly, the operation temperature may be predicted using Equation 5 if the operation resistance is known. Here, $R_0$ refers to the resistance of the platinum hot wire at 0□, and "a" refers to the temperature resistance coefficient, for example, 0.0039092/□ in case of platinum.

All numerical data necessary to calculate the convective heat transfer coefficient h may be obtained through the above processes.

Figure 5:
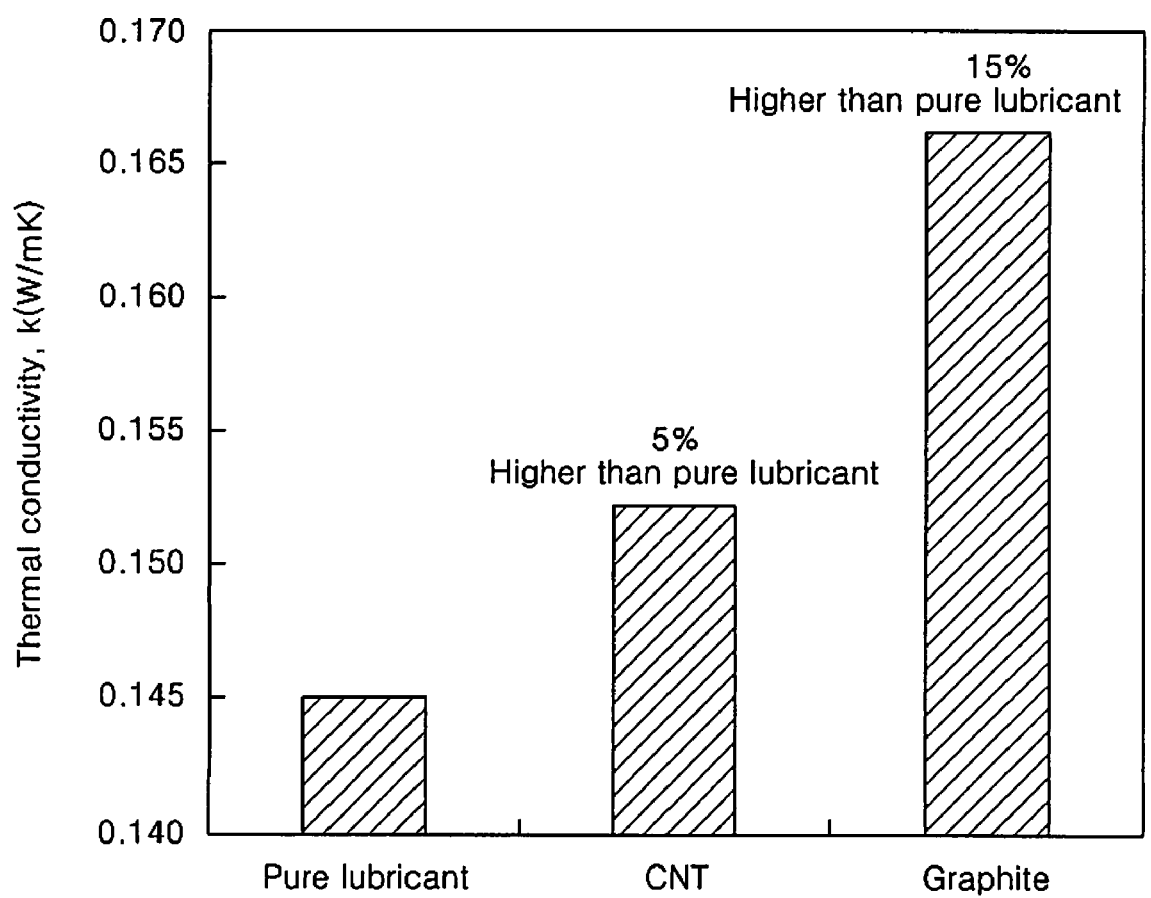
FIG. 5 is a view illustrating thermal conductivities measured at room temperature using an abnormal hot wire method according to an exemplary embodiment.

FIG. 5 is a view illustrating thermal conductivities measured at room temperature using an abnormal hot wire method according to an exemplary embodiment.

Referring to FIG. 5, three types of samples are prepared to perform an experiment for verifying convective heat transfer, such as a pure lubricant, a nano-lubricant mixed with carbon-nano-tube (CNT), and a nano-lubricant mixed with graphite. In case of the nano-lubricant, mixed concentration of each of the two types of nano-lubricants is 0.5% by volume percent.

The nano-lubricant mixed with CNT exhibited increase of thermal conductivity by about 5% compared to the pure lubricant, the nano-lubricant mixed with graphite exhibited increase of thermal conductivity by about 15% compared to the pure lubricant. The nano-lubricant mixed with graphite showed increase in thermal conductivity by more than 10% than the nano-lubricant mixed with CNT.

The increase of thermal conductivity by 15% in the mixed concentration of 0.5 vol. % corresponds to a high increasing rate compared to the results of existing experiments.

Figure 6:
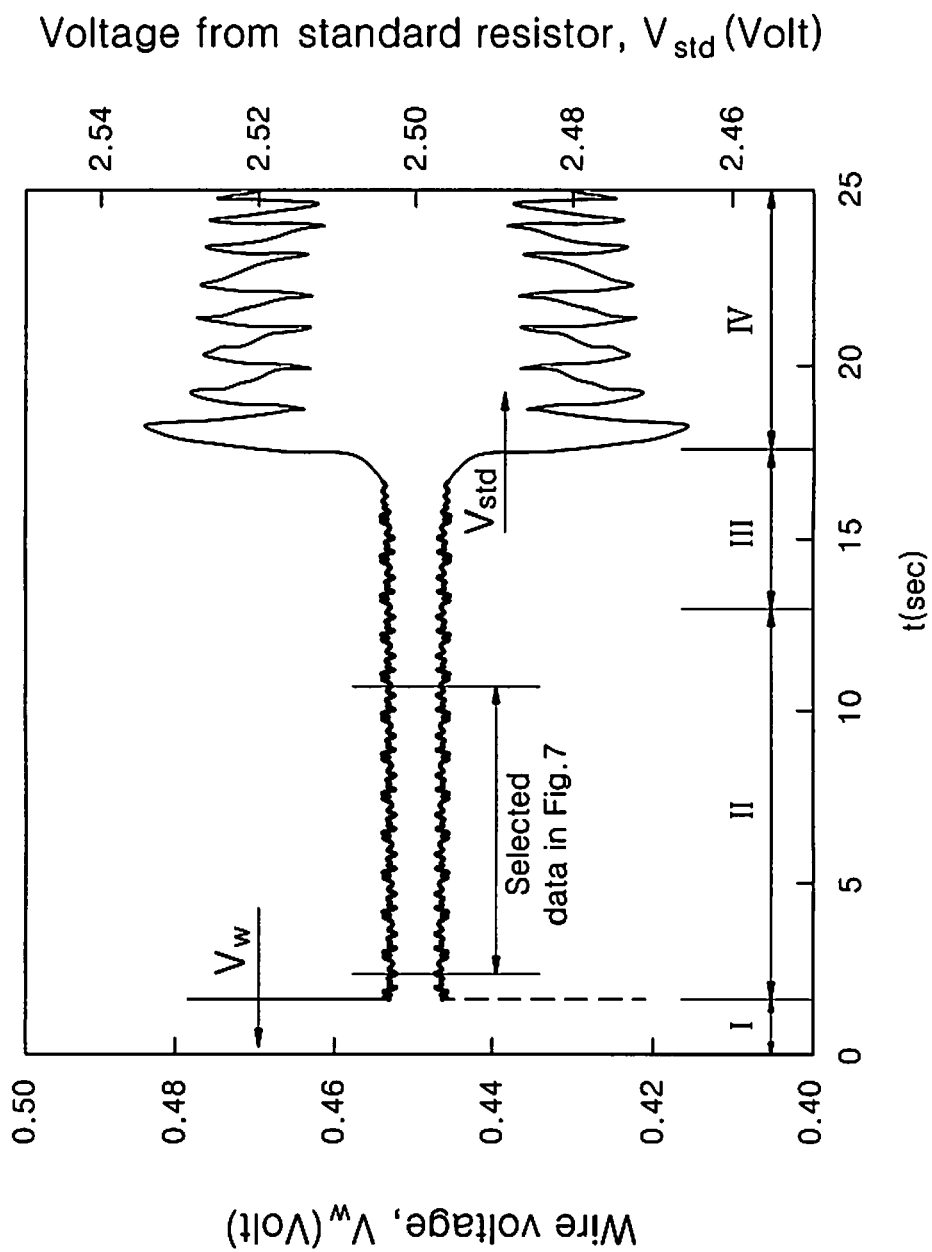
FIG. 6 is a view illustrating an example of voltage signals acquired from a standard resistor and a hot wire according to an exemplary embodiment.

FIG. 6 is a view illustrating an example of voltage signals acquired from a standard resistor and a hot wire according to an exemplary embodiment.

Referring to FIG. 6, left, vertical axis refers to a hot wire, right, vertical axis to a signal from the standard resistor, and horizontal axis to time.

The sum of the two signals flowing over the entire time during which the measurement is made is 3 volts. This is why the voltage of 3 volts supplied from a power supply has been split according to the relative magnitude of the two resistors. That is, when the platinum hot wire is heated with the resistance of the standard resistor constant, so that the resistance of the platinum hot wire increases, the voltage across the platinum hot wire increases but the entire voltage of 3 volts remains constant, and therefore, the voltage across the standard resistor decreases. On the contrary, the voltage across the platinum hot wire decreases and the voltage across the standard resistor increases when the platinum hot wire is cooled.

Accordingly, variation of the voltage applied across the platinum means variation of resistance, i.e. variation of operation temperature.

In section I, from initiation of the experiment to 1.6 seconds, current alone flows across the hot wire without fluid flow.

In section II, from 1.6 seconds to 13 seconds, horizontal voltage signals are obtained while the fluid passes through the pipe with the hot wire cooled. Accordingly, section I includes cooling alone by natural convection and therefore exhibits higher temperature of the hot wire and higher resistance than section II which includes forced convective fluid flow, thus exhibiting higher voltage.

The signal being nearly constant during section II means the velocity of the fluid discharged during section II is substantially constant.

In section III, less horizontal signals are shown than in section II, and these signals is are generated when the fluid completely passes trough the long pipe and some of the fluid remaining in the rubber tube and the short pipe pass through the platinum hot wire.

In section IV, which appears 17 seconds after the experiment initiated, the saw-toothed signals are appeared. These saw-toothed signals are generated when some of the fluid remaining on the wall surfaces inside the pipe are accumulated to form large drops and dripped on and off from the outlet. This may be easily understood by imagining that a lubricant flows down from a container or tube at the final moment. During this section, the hot wire repeats cooling and heating by the lubricant dripped on and off, and therefore, the resistance of the hot wire alternately increases and decreases. Therefore, the relative resistance of the hot wire varies with respect to the standard resistor, and therefore, the voltage across the hot wire and the standard resistor appears as a vibrating wave.

Figure 7A:
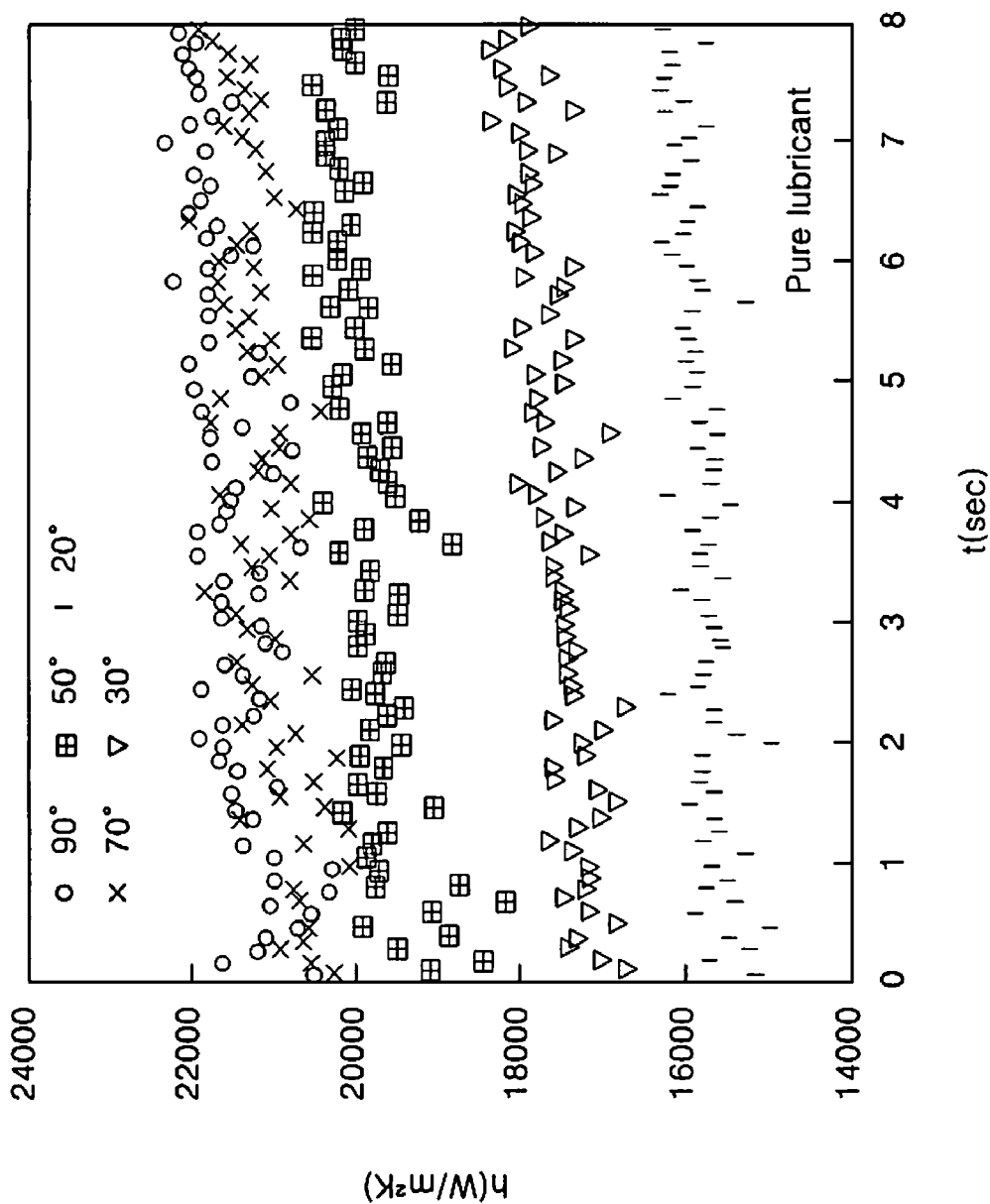
Figure 7B:
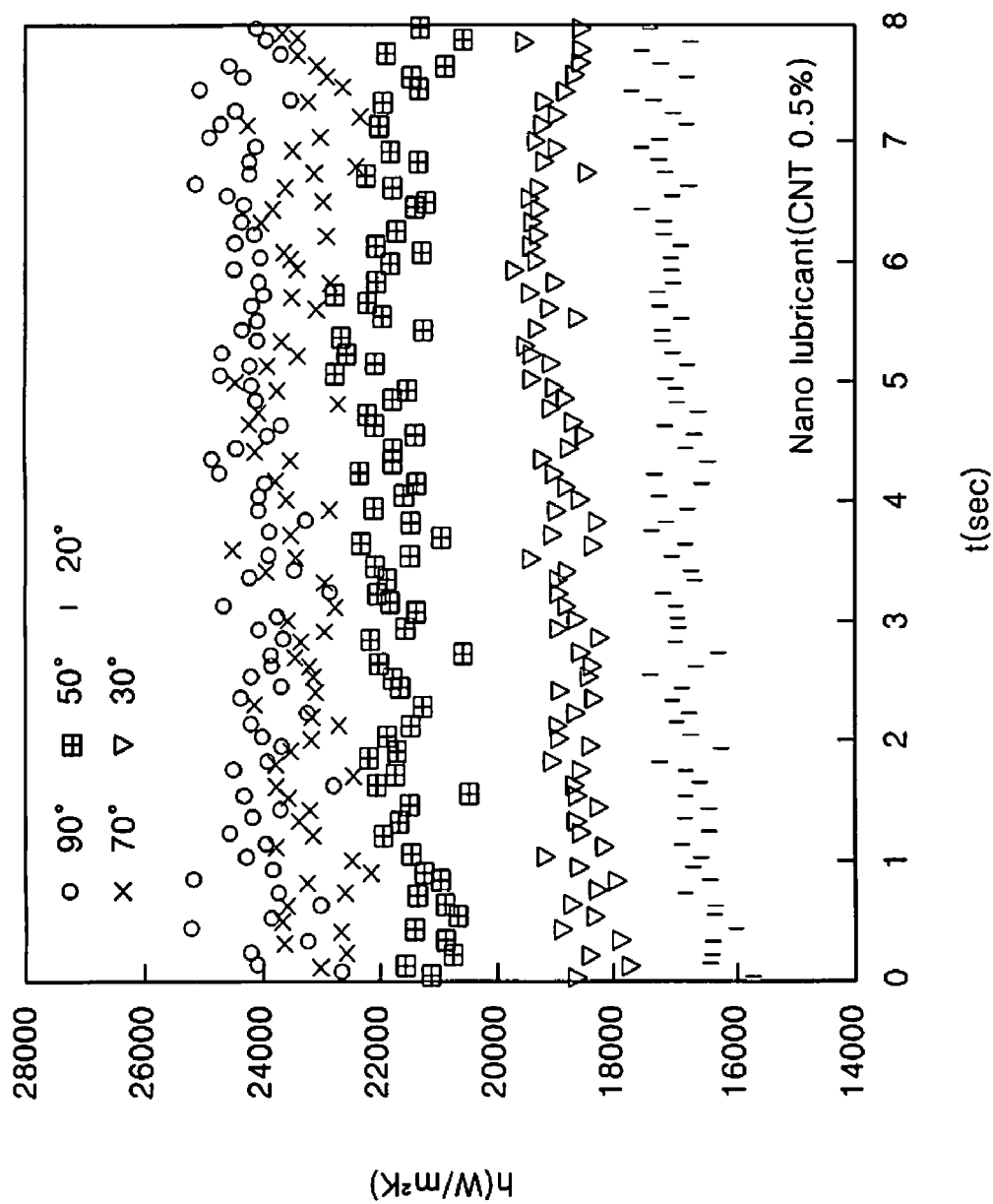

FIGS. 7A, 7B, and 7C shows results of an experiment according to an exemplary embodiment, which is made with respect to three types of samples including another pure lubricant, a nano-lubricant mixed with CNT, and a nano-lubricant mixed with graphite, with the slope of the long pipe changed.

In FIG. 6, each and every convective heat transfer coefficient is plotted in FIG. 7 for each and every moment using the data at 8 seconds which is most stable in section II of FIG. 7. Referring to FIGS. 7A, 7B, and 7C, "90°" refers to a case where the long pipe is perpendicular to the ground, and "20°" refers to a case where the long pipe is nearly horizontal to the ground. For the whole samples, the convective heat transfer coefficients are not constant but slightly increase. This is why the fluid which has been kept stationary is accelerated as time goes on which in turn increases the flow velocity, and therefore, the convective heat transfer coefficients are increased.

Evident differences appear between the convective heat transfer coefficients as the velocity of fluid increases by varying the slope of the long pipe.

Figure 8:
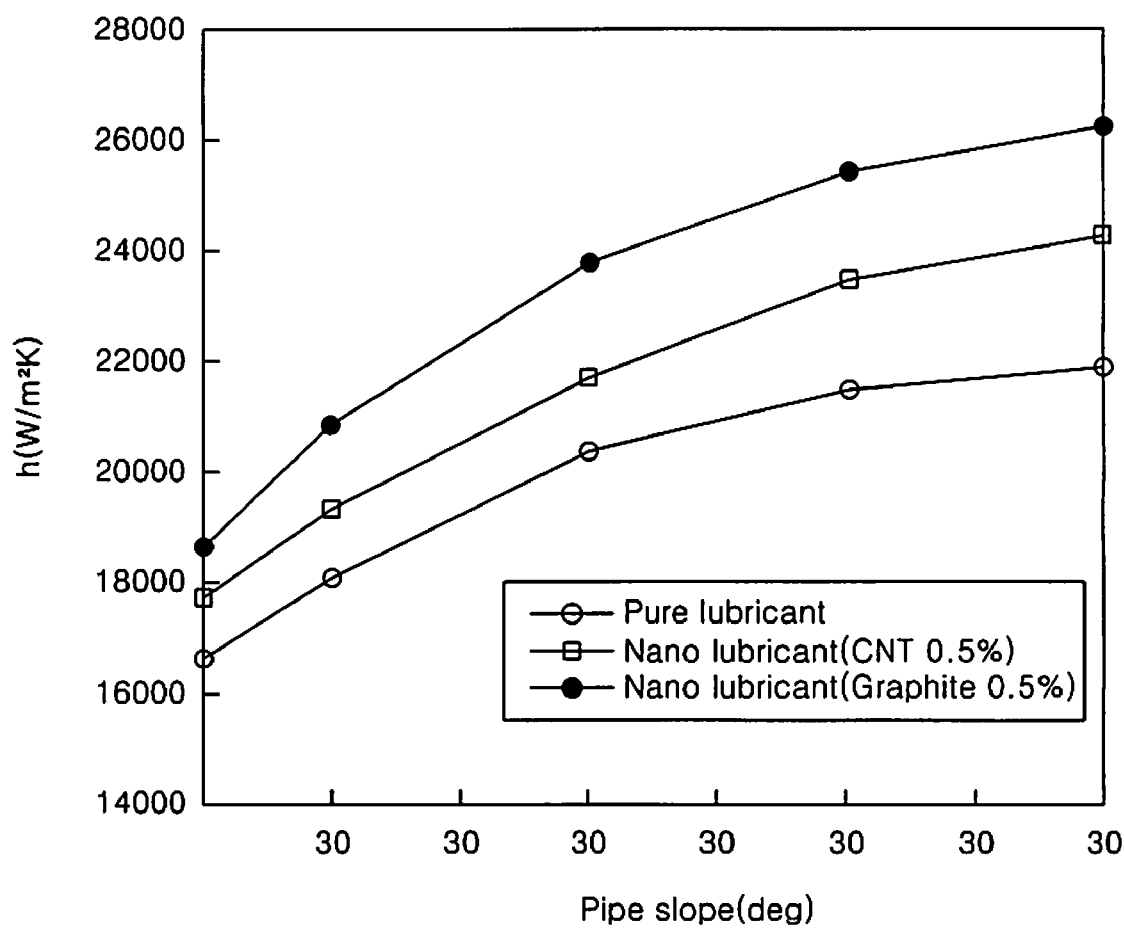
FIG. 8 is a view illustrating convective heat transfer coefficients that are calculated by averaging the data for 8 seconds shown in FIGS. 7A, 7B, and 7C.

FIG. 8 is a view illustrating convective heat transfer coefficients that are calculated by averaging the data for 8 seconds shown in FIGS. 7A, 7B, and 7C.

It can be seen from FIG. 8 that evident differences appear in the convective heat transfer coefficients between the three samples and the convective characteristics of the nano-lubricants are high when the angles of the slopes are the same.

In case of the heat transfer evaluation apparatus of the nano-fluid according to the exemplary embodiments, the same angle means the same pumping power because the gravity is only external power that is exerted on this system.

Although the present disclosure has been described with reference to certain exemplary embodiments thereof, it will be understood by those skilled in the art that a variety of modifications and variations may be made to the present disclosure without departing from the spirit or scope of the present disclosure defined in the appended claims, and their equivalents.

What is claimed is:

1. A heat transfer evaluation apparatus of a nano-fluid comprising:
    a long pipe formed as a circular pipe;
    a rubber tube connected to one end of the long pipe to surround the outer surface of the long pipe;
    a short pipe communicated through the rubber tube; and
    a hot wire sensor formed of a metal hot wire at one end of the short pipe.

2. The heat transfer evaluation apparatus of a nano-fluid of claim 1, wherein the metal hot wire is a platinum hot wire.

3. The heat transfer evaluation apparatus of a nano-fluid of claim 2, wherein a thick copper wire is connected to both ends of the platinum hot wire.

4. The heat transfer evaluation apparatus of a nano-fluid of claim 3, wherein the copper wire is attached onto the outer surface of the short pipe so that the platinum hot wire is located cross the center of the inner diameter of the short pipe.

5. A heat transfer evaluation apparatus of a nano-fluid comprising:
    a long pipe formed as a circular pipe;
    a rubber tube connected to one end of the long pipe to surround the outer surface of the long pipe;
    a short pipe communicated through the rubber tube; and
    a hot wire sensor formed of a metal hot wire at one end of the short pipe;
    a standard resistor electrically connected to the hot wire sensor; and
    a power supply supplying a current to the standard resistor, wherein the hot wire sensor includes a data acquisition device that may acquire measured data.

6. The heat transfer evaluation apparatus of a nano-fluid of claim 5, wherein the standard resistor is connected in series with a platinum hot wire.

* * * * *